United States Patent [19]

Messick et al.

[11] 4,422,903

[45] Dec. 27, 1983

[54] ANHYDROUS ETHANOL DISTILLATION METHOD AND APPARATUS

[75] Inventors: John R. Messick; William R. Ackley; George D. Moon, Jr., all of Cincinnati, Ohio

[73] Assignee: Raphael Katzen Associates International Inc., Cincinnati, Ohio

[21] Appl. No.: 234,771

[22] Filed: Feb. 17, 1981

[51] Int. Cl.³ .................. B01D 3/36; C07C 31/08; C07C 29/80
[52] U.S. Cl. ...................... 203/19; 203/22; 203/23; 203/25; 203/27; 203/39; 203/43; 203/52; 203/68; 203/69; 203/70; 203/88; 203/98; 203/74; 203/75; 203/77; 203/80; 203/DIG. 13; 203/DIG. 9; 203/DIG. 19; 202/154; 202/155; 202/156; 202/159; 202/173; 202/174; 202/180
[58] Field of Search ............... 203/19, DIG. 13, 21, 203/25, 43–46, 26, 23, 49, 22, 24, 39, 27, 88, 73, 85, 99, 91, 94, 98, DIG. 9, DIG. 19, 50, 52, 68–70; 202/180, 159, 154, 158, 172, 173, 174, 156; 435/161; 44/53, 56; 568/916

[56] References Cited

U.S. PATENT DOCUMENTS

| | | | |
|---|---|---|---|
| 1,702,495 | 2/1929 | Clapp . | |
| 1,822,454 | 9/1931 | Ricard et al. . | |
| 1,860,554 | 5/1932 | Ricard et al. . | |
| 2,017,067 | 10/1935 | Kraft . | |
| 3,445,345 | 5/1969 | Katzen et al. | 203/25 |
| 3,990,952 | 11/1976 | Katzen et al. | 203/36 |
| 4,161,429 | 7/1979 | Baiel et al. | 203/18 |
| 4,217,178 | 8/1980 | Katzen et al. | 203/19 |
| 4,256,541 | 3/1981 | Muller et al. | 203/19 |
| 4,306,940 | 12/1981 | Zenty | 203/25 |
| 4,306,942 | 12/1981 | Brush et al. | 203/25 |
| 4,309,254 | 1/1982 | Dahlstrom et al. | 203/19 |
| 4,340,446 | 7/1982 | Crawford | 203/DIG. 13 |
| 4,372,822 | 2/1983 | Muller | 203/19 |

FOREIGN PATENT DOCUMENTS 2346450 10/1977 France .

OTHER PUBLICATIONS

Grain Motor Fuel Alcohol Technical and Economic Assessment Study, U.S. Dept. of Energy, Jun. 1979, pp. 52–61.
Chemical Process Industries, Shreve, 1945, pp. 653–654.
Elements of Fractional Distillation, Robinson and Gilliland, 1950, pp. 168–170.
"Controlled Heat Integrated Distillation Columns", Tyreus et al., Chemical Engineering Progress, Sep. 1976, pp. 59–66.

Primary Examiner—Wilbur L. Bascomb, Jr.
Attorney, Agent, or Firm—Merriam, Marshall & Bicknell

[57] ABSTRACT

An improved distillation method and apparatus are provided for recovering anhydrous ethanol from fermentation or synthetic feedstocks. The system includes at least one stripper-rectifier tower, a dehydrating tower, and an azeotropic agent stripping tower. Substantial energy savings are realized by operating the dehydrating tower, and preferably also the azeotropic agent stripping tower, at a higher pressure than the stripper-rectifier tower and by condensing the overhead vapors from the dehydrating tower (or dehydrating tower and azeotropic agent stripping tower) to provide the heat required in the stripper-rectifier tower. In a preferred embodiment, two stripper-rectifier towers are used, one operating at a higher pressure than the other, in which case the higher pressure tower is heated as just described and the overhead vapors from the higher pressure tower are condensed to supply the heat required in the lower pressure tower. Further energy savings are accomplished by preheating the feedstock by means of the heat contained in the stripper-rectifier tower overhead (the lower pressure stripper-rectifier tower in the case where two such towers are used) and also by the heat contained in the stripper-rectifier bottoms.

19 Claims, 2 Drawing Figures

ANHYDROUS ETHANOL DISTILLATION METHOD AND APPARATUS

This invention relates to a novel and improved integrated distillation system for recovering anhydrous ethanol from fermentation or synthetic feedstocks. Although not so limited, the invention is of particular importance in the production of anhydrous ethanol for use as a component of motor fuel.

BACKGROUND OF THE INVENTION

The use of anhdyrous ethanol (99.5 to 99.8 vol.% ethanol) has become an important consideration as a means of saving gasoline produced from high-cost crude oil. It is well-known that up to 20 percent anhydrous ethanol can be blended with gasoline to obtain a relatively high octane antiknock fuel which can be used for internal combustion engines. With some engine modification, either anhydrous or hydrous ethanol can be used as the fuel directly.

Growing requirements for anhydrous ethanol for use in motor fuel gasoline blends require systems that operate with minimum energy consumption and that are also reliable in continuous operation. Although blending of ethanol with gasoline has been practiced commercially to some extent during the past forty years, the use of ethanol in such blends has been limited because of the relatively high costs of production.

The conventional distillation system for recovering motor fuel grade anhydrous ethanol from a dilute feedstock, such as fermented beer or synthetic crude alcohol, utilizes three towers, each operated at substantially atmospheric pressure and separately heated with steam. In the first tower the feedstock containing, for example, 6 to 10 vol.% ethanol is subjected to a preliminary stripping and rectifying operation in which the concentration of water is materially reduced. The overhead vapors are condensed at atmospheric pressure with cooling water. A portion of the condensate is returned to the first tower as reflux, and the balance is withdrawn as a concentrated ethanol stream containing on the order of 95 vol.% ethanol, thereby approaching the ethanol-water azeotrope composition of about 97 vol.% ethanol. The concentrated ethanol stream is next subjected to azeotropic distillation in the second or dehydrating tower using a suitable azeotropic or entraining agent, usually benzene or a benzene-heptane mixture. This results in removal of most of the remaining water, and the desired motor fuel grade anhydrous ethanol product is recovered as a bottoms product from the dehydrating tower. The third tower of the system comprises an azeotropic agent stripping tower in which the azeotropic agent is recovered from the water-rich phase following condensation and decantation of the azeotropic overhead stream from the dehydrating tower.

A key factor in the high operating cost of the above-described conventional distillation system is the high thermal energy requirements of the system, particularly steam consumption. Certain proposals have been made in the prior art to reduce the thermal energy requirements of the conventional system. For example, in 1931–32 the Ricard et al U.S. Pat. Nos. 1,822,454 and 1,860,554 disclosed the use of higher pressures in the first tower than in the other towers and the condensation of the high pressure overhead vapors from the first tower to supply heat to the other towers. In the Katzen et al U.S. Pat. No. 4,217,178 even further savings are obtained by combining the multi-pressure level and heat re-use concept with a particular feedstock preheating sequence. However, the energy savings which can be realized by such prior art proposals sometimes fall short of the economies required under present day conditions of high energy costs. Moreover, pressurized operation of the first tower is not always feasible because of its harmful effects on soluble or insoluble components of the feedstock.

SUMMARY OF THE INVENTION

Accordingly, the principal object of the present invention is to provide an improved distillation method and apparatus for recovering anhydrous ethanol from fermentation or synthetic feedstocks which permits increased energy savings without sacrificing operating efficiency or product quality.

In general, the foregoing objective is achieved by pressurized operation of the dehydrating tower, and preferably also the azeotropic agent stripping tower, so that the overhead vapors from these towers can be used as the heat source for one or more lower pressure stripper-rectifier towers. This method makes it possible to obtain the advantages of the multi-pressure level and heat re-use concept while avoiding excessive pressurization of the stripper-rectifier tower which can cause undesirable polymerization and degradation of certain components of the feedstock. In the preferred embodiment of the invention dual towers are provided for initial stripping and rectification of the feedstock and are operated at successively lower pressures than the dehydrating tower and the azeotropic agent stripping tower so as to obtain the heat economy benefits of a unique triple pressure system. In addition, the invention also achieves further heat economy by preheating the feedstock in sequence with overhead vapors and bottoms associated with the stripping and rectification section of the system.

As a result, the steam consumption in the improved system of the present invention is reduced to the order of 14 to 18 pounds per U.S. gallon of anhydrous ethanol product, dependent upon the ethanol content of the feedstock, which represents an energy saving of from about 25% to about 60% over the conventional system and also represents a substantial additional energy saving over the systems described in the aforementioned U.S. Pat. Nos. 1,822,454, 1,860,554, and 4,217,178.

From an equipment viewpoint, the preferred form of the invention utilizes in the stripper section of the stripper-rectifier towers the internal tower design and mode of operation described in British Pat. No. 1,310,544 and Canadian Pat. No. 876,620 which are incorporated herein by reference. With the baffle tray construction and critical vapor velocity relationships described in those patents the accumulation of scale and residue is retarded and the trays are to a large extent self-cleaning so that interruption of operation is held to a minimum.

Other features and advantages of the invention will be seen from the subsequent detailed description in conjunction with the accompanying drawings.

DETAILED DESCRIPTION

Figure 1:
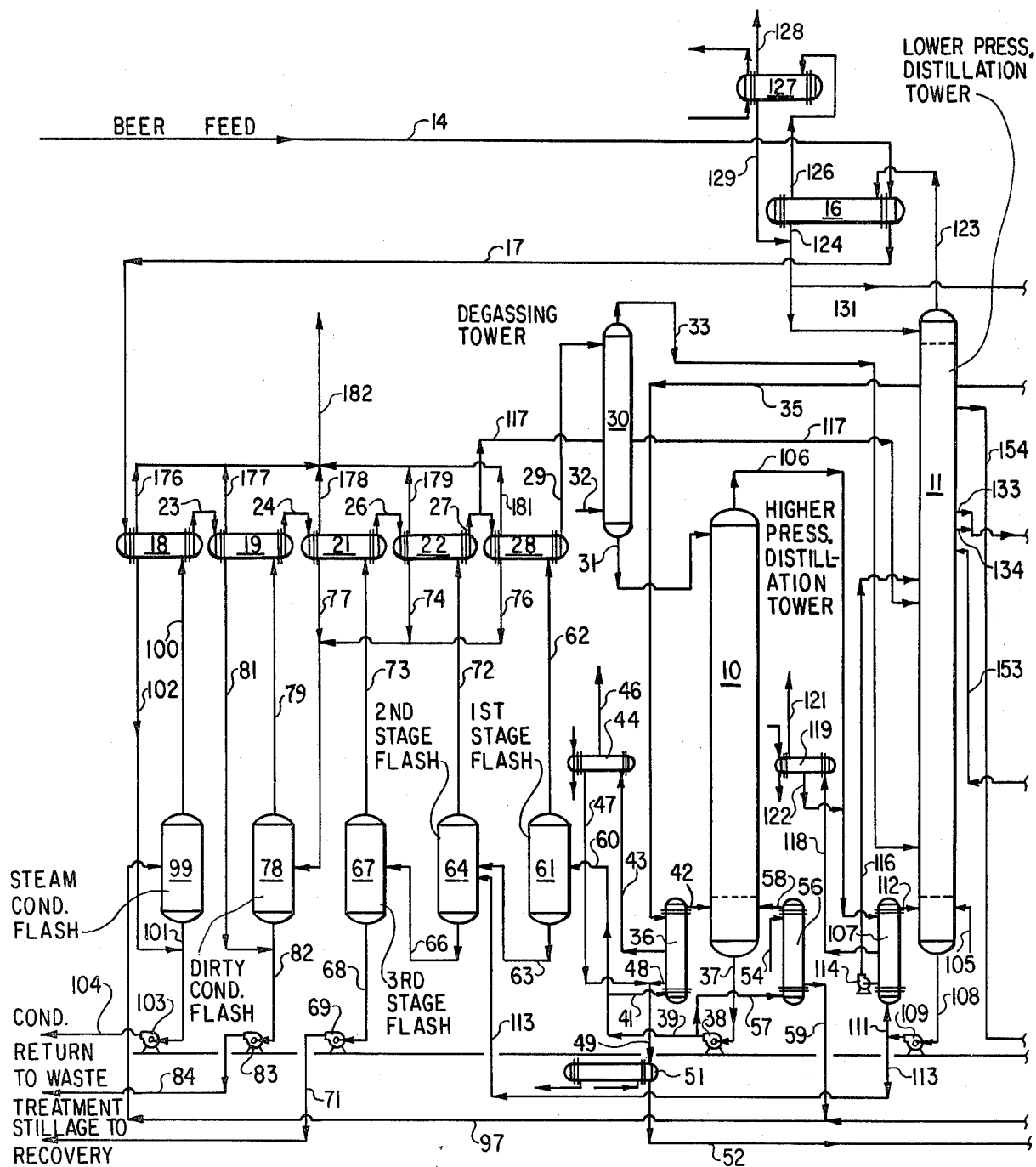
FIG. 1 is a diagrammatic flow sheet showing a portion of a distillation system comprising a specific embodiment of the present invention for processing a feedstock containing suspended solids.
Figure 2:
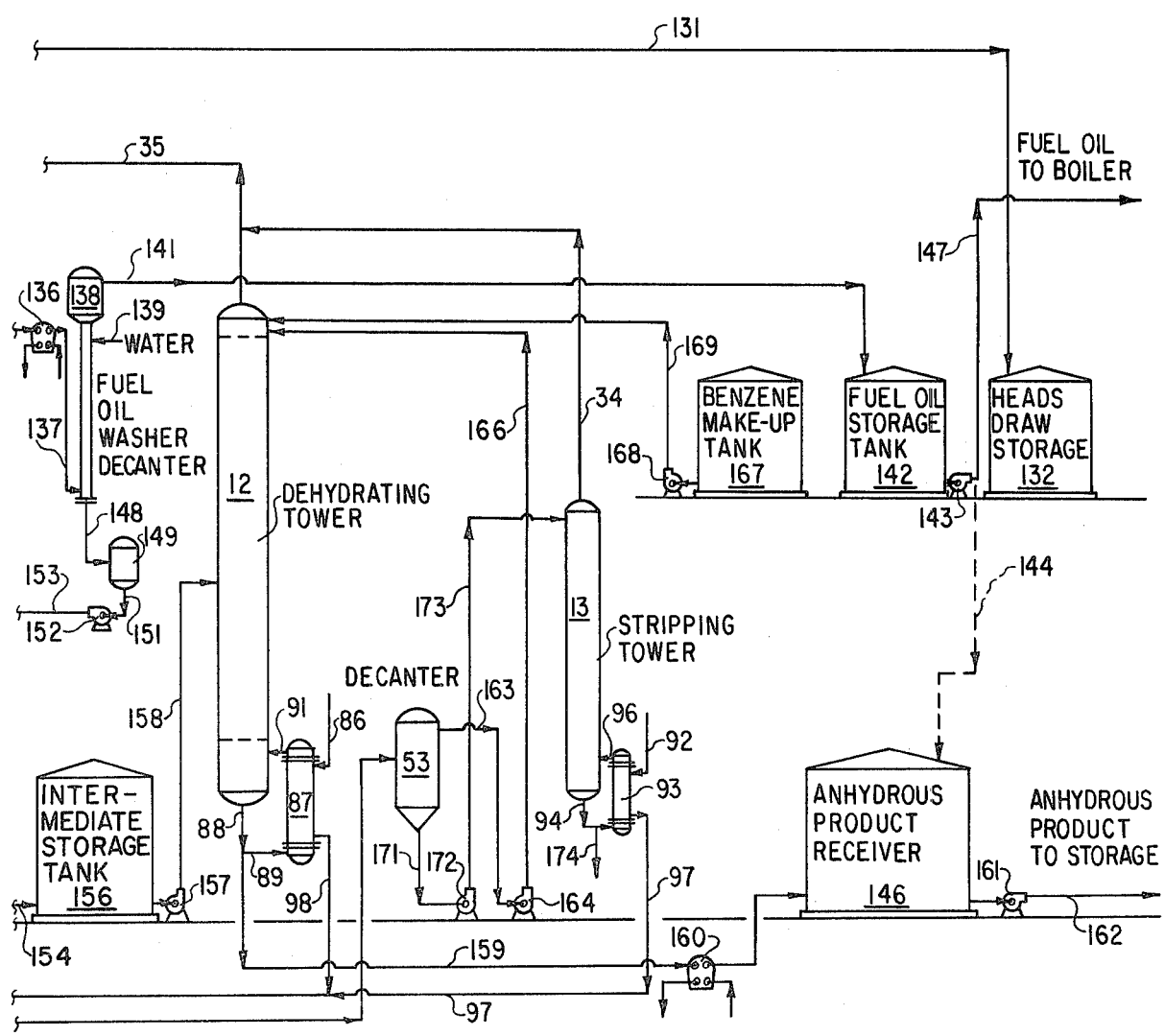
FIG. 2 is a continuation of the flow sheet of FIG. 1 which shows the remainder of the distillation system.

Although any suitable fermented or synthetic feedstock can be used in practicing the invention, the distillation system illustrated in FIGS. 1 and 2 utilizes a fermented beer feedstock obtained from starch conversion to fermentable sugar materials or directly from fermentable sugar materials. The feedstock may contain from about 0.5 to about 20 wt.% ethanol (usually from about 3 to about 10 wt.%), up to about 1 wt.% organic impurities, and up to about 10 wt.% dissolved and suspended solids. The flash vapor-liquid heat exchange arrangement, as described below in connection with FIG. 1, for recovery of heat from the stripper-rectifier tower bottoms streams is particularly suited for a feedstock containing suspended solids, but if the feedstock is substantially free of suspended solids, a liquid-liquid heat exchange arrangement can be used.

The stripping and rectification section utilizes a first stage distillation tower 10 and a second stage distillation tower 11, and the system further includes a pressurized dehydrating or azeotropic distillation tower 12 and a pressurized azeotropic agent stripping tower 13 both of which are operated at higher pressures than the towers 10 and 11.

The fermented beer at a temperature of from about 80° F. to about 95° F. is introduced through line 14 and is preheated in successive stages by passing through a condenser-preheater 16 and then through line 17 and a series of heat exchangers or condenser-preheaters 18, 19, 21, and 22 interconnected by lines 23, 24, and 26, as described in more detail below. The partially preheated feedstock leaves the heat exchanger 22 through a line 27 is then split into two feed streams of unequal size. One feed stream passes through the line 27 to a heat exchanger or condenser-preheater 28 where the final preheat is provided. This feed stream is the larger of the two and preferably comprises more than 50 wt.% but not usually more than about 70 wt.% of the total feed. The preheated feed stream then passes through a line 29 to a degassing vessel 30 where dissolved carbon dioxide resulting as a by-product of the fermentation is removed. In the case of synthetic feedstock from direct hydration synthesis, dissolved ethylene would be removed in vessel 30. The degassed and further preheated feed stream then passes through a line 31 to the top of the higher pressure tower 10 which in this embodiment of the invention operates as an ethanol stripper only. Dissolved gas is removed from the feed stream in the degassing vessel 30 by means of a small amount of steam introduced through a line 32 and the resultant stream is passed through a line 33 to a lower portion of the lower pressure stripper-rectifier tower 11.

Heat is supplied to the tower 10 by means of the combined overhead vapors from the dehydrating tower 12 and the azeotropic agent stripping tower 13 which are operated at a higher pressure than the tower 10. Overhead vapors from the tower 13 are removed through a line 34 and are combined with overhead vapors removed from the tower 12 through a line 35. The combined vapors pass through line 35 to a condenser-reboiler 36, and a portion of the bottoms stream from the tower 10 is recycled through the condenser-reboiler 36 by means of a line 37, a pump 38, and lines 39, 41, and 42. Uncondensed vapors from the sheel side of the condenser-reboiler 36 are passed through a line 43 to a water cooled vent condenser 44, and uncondensible gases are vented through a line 46. Condensate from the vent condenser 44 passes through a line 47 and is combined with condensate withdrawn from the shell side of the condenser-reboiler 36 through a line 48. The combined condensate passes through a line 49 to a water cooled cooler 51 and thence by a line 52 to a decanter 53.

In the event that additional heat is required in the tower 10, steam may be supplied through a line 54 to the shell side of an auxiliary reboiler 56, and another portion of the bottoms stream from the tower 10 is recycled through the tube side of the reboiler 56 by means of line 37, a line 57, and a line 58. Steam condensate is removed from the reboiler 56 by a line 59.

The non-recycled portion of the bottom stream from the tower 10 passes through a line 60 to a first stage flash drum 61 where flash vapors are removed overhead and passed through a line 62 and to the heat exchanger 28. The bottoms from the flash drum 61 are passed successively through a line 63 to a second stage flash drum 64 and thence through a line 66 to a third stage flash drum 67 and are finally withdrawn from the flash drum 67 through a line 68 by a pump 69 which discharges through a line 71 to a stillage recovery section (not shown) where evaporation of the water content may be effected to recover valuable proteinaceous materials.

Flash vapors from the flash drums 64 and 67 are removed overhead and passed through lines 72 and 73 to the heat exchangers 22 and 21, respectively. Condensates from the heat exchangers 22 and 28 are withdrawn through lines 74 and 76, respectively, and are combined with condensate withdrawn from the heat exchanger 21 through a line 77. The combined condensates are introduced by the line 77 to a dirty condensate flash drum 78, and further heat is recovered by removing flash vapors overhead through a line 79 and passing them to the heat exchanger 19. The condensate from the heat exchanger 19 is withdrawn through a line 81 and is combined with the residual bottoms withdrawn from the flash drum 78 through a line 82, the combined stream being discharged by a pump 83 through a line 84 to a waste treatment section (not shown).

Additional heat recovery is also obtained from the hot steam condensates from the system. Thus, the dehydrating tower 12 is heated by steam introduced through a line 86 to a reboiler 87, and a portion of the bottoms stream withdrawn from the tower 12 by a line 88 is recycled through the reboiler 87 by means of lines 89 and 91. Similarly, the azeotropic agent stripping tower 13 is heated by steam introduced through a line 92 to a reboiler 93, and a bottoms stream from the tower 13 is recycled through the reboiler 93 by means of lines 94 and 96. The steam condensate from the reboiler 93 is removed through a line 97 and is combined with steam condensate withdrawn from the reboiler 87 through a line 98 and also with steam condensate in the line 59 from the auxiliary reboiler 56 when the latter is required. The combined steam condensate stream passes through the line 97 to a steam condensate flash drum 99 where overhead vapors are removed through a line 100 and passed to the heat exchanger 18. Bottoms from the flash drum 99 are removed through a line 101 and are combined with condensate removed from the heat exchanger 18 through a line 102. The combined condensate is returned to the boiler (not shown) by a pump 103 and a condensate return line 104. Uncondensible gases or vapors from the heat exchangers 18, 19, 21, 22, and 28 are removed through lines 176, 177, 178, 179, and 181, respectively, and are vented to the atmosphere through a line 182.

Overhead vapors from the tower 10 containing a relatively weak concentration of ethanol are removed through a line 106 and are passed to a condenser-reboiler 107 for supplying heat to the second stripper-rectifier tower 11 which operates at a lower pressure than the tower 10. If needed, additional steam can be added directly to the tower 11 through a line 105 for start-up and balancing purposes. A bottoms stream is withdrawn from the tower 11 through a line 108 and a pump 109, and a portion of the bottoms stream is recycled through the condenser-reboiler 107 by means of lines 111 and 112. The remainder of the bottoms stream passes from the pump 109 through a line 113 to the second stage flash drum 64 for supplying additional preheat to the incoming feed.

The condensate from the condenser-reboiler 107 is supplied by a pump 114 through a line 116 and is introduced into the stripper-rectifier tower 11 slightly above the mid-section of the tower as one of the primary feed streams to this tower. The other primary feed stream is the remaining portion of the split feed which passes from line 27 through a line 117 directly to the stripper-rectifier tower 11 where it is introduced at a point slightly below the point of introduction of the other primary feed stream through the line 116. The feed stream introduced through the line 117 is the smaller of the two split feed streams and preferably comprises less than 50 wt.% but generally not less than about 30 wt.% of the total feed. Uncondensed vapors from the condenser-reboiler 107 are passed through a line 118 to a water cooled vent condenser 119, and uncondensible gases are vented through a line 121 while condensate from the vent condenser 119 is returned by a line 122 to the line 106 which supplies overhead vapors from the tower 10 to the condenser-reboiler 107.

The stripper-rectifier tower 11 may be considered as having four zones. The lowest zone functions as a stripping section to remove ethanol from the aqueous ethanol feed streams introduced into the tower 11. In the next higher zone the fusel oil impurities are concentrated to permit their removal as a side stream. In the next higher zone the aqueous alcohol is concentrated to about 190° U.S. proof (95 vol.%) and is removed as a spirits draw for further concentration in the dehydrating tower 12. The uppermost zone comprises a pasteurization section in which the low boiling impurities are concentrated to permit their removal from the system as a heads draw.

Overhead vapors from the tower 11 pass through a line 123 to the condenser-preheater 16 to provide the initial preheat for the feedstock. Condensate from the condenser-preheater is returned through a line 124 as reflux to the top of the tower 11. Uncondensed vapors from the condenser-preheater 16 pass through a line 126 to a water cooled vent condenser 127 where uncondensible gases are vented through a line 128 and any condensate is returned through a line 129 to the reflux return line 124. A small heads draw, e.g. on the order of 1 to 2% of the total anhydrous ethanol production, is taken from the reflux return line 124 and is passed through a line 131 to a storage tank 132. Since the overhead from the tower 11 contains the low-boiling impurities in the feedstock, particularly acetaldehyde, the continuous heads draw through line 131 removes these impurities from the system and avoids their accumulation and adverse effects on the quality of the ethanol product. However, this stream has significant fuel value and may be sent from the storage tank 132 to the plant boiler as a fuel source.

Higher boiling impurities such as alcohols and esters (fusel oils) are formed as extraneous products of the fermentation (or synthesis) process, and in the present invention these impurities are removed as one or more liquid side streams 133 and 134 from an intermediate portion of the stripper-rectifier tower 11 above the points of introduction of the feed streams through the lines 116 and 117. The fusel oil draws are normally made at an alcohol concentration between about 100° and about 160° U.S. proof. The side streams are combined and passed through a water cooled cooler 136 and are then introduced through a line 137 to the lower end of a fusel oil washer-decanter 138. The cooled mixed side stream is washed countercurrently with cold water introduced at 139, and the fusel oils are decanted as an upper layer which is withdrawn through a line 141. The separated fusel oil layer also has significant fuel value and is passed to a storage tank 142 from which it may be pumped by a pump 143 through a line 144 for blending into the anhydrous ethanol product in receiver 146 or through a line 147 to the plant boiler as a fuel source. The lower aqueous layer containing ethanol washed out of the fusel oil passes through a line 148 to an accumulator drum 149 and is withdrawn through a line 151 and is pumped by a pump 152 through a line 153 to a side entry point somewhat above the main feed entry points (at lines 116 and 117) of the stripper-rectifier tower 11 but somewhat below the side stream withdrawal points (at lines 133 and 134).

An intermediate spirits product (95 vol.% ethanol) is removed as a liquid side stream somewhat below the top of the stripper-rectifier tower 11 and is passed through a line 154 to an intermediate storage tank 156. The spirits draw stream becomes the feed stream for the dehydrating tower 12, but the intermediate storage tank 156 acts as an accumulator in the process. Thus, if a system upset occurs in the dehydrating tower 12, the stripper-rectifier towers 10 and 11 can continue in operation in the normal manner, and the ethanol product is accumulated in the storage tank 156 until the tower 12 has been restored to an acceptable condition.

The spirits product (190° U.S. proof) is fed from the storage tank 156 by a pump 157 through a line 158 to the central section of the dehydrating tower 12. This tower is an azeotropic distillation tower producing anhydrous ethanol as its bottom product and utilizing an azeotropic agent, preferably benzene, although other azeotreopic agents such as heptane, a benzene-heptane mixture or cyclohexane, may also be used. The non-recycled portion of the bottoms stream from the tower 12 passes through a line 159 and a water-cooled product cooler 160 to the product receiver 146. From the receiver 146 the ahydrous ethanol product is pumped to storage by a pump 161 and a line 162.

The overhead product from the dehydrating tower 12, which is close in composition to the minimum boiling ternary azeotrope of ethanol, water, and azeotropic agent, passes through the line 35 to the condenser-reboiler 36, and the resultant condensate is cooled in the cooler 51 and passed to the decanter 53, as previously described, where the heterogeneous azeotrope splits into two phases. The upper layer from the decanter 53, which is rich in azeotropic agent and ethanol, is withdrawn through a line 163 and is returned by a pump 164 through a line 166 as reflux to the top of dehydrating tower 12. When required, make-up azeotropic agent from a tank 167 may be added to the tower 12 through a pump 168 and a line 169. The decanter bottom layer, a water-rich layer containing some ethanol and azeotropic agent, is withdrawn through a line 171 and is pumped by a pump 172 through a line 173 to the top of the azeotropic agent stripping tower 13. Overhead vapors from the tower 13 pass through line 34 which joins line 35, and the combined vapors from the towers 12 and 13 pass to the condenser-reboiler 36, as heretofore described. The bottoms product from the tower 13 is a water stream which is essentially free of azeotropic agent and ethanol, and the non-recycled portion of the bottoms stream is withdrawn from line 94 and discarded to waste through a line 174.

From the foregoing it will be seen that the invention accomplishes a substantial reduction in energy consumption by recovering and utilizing to the fullest extent the heat content of various process streams of the system. Thus, the dehydrating tower 12 and the azeotropic agent stripping tower 13 are operated at an elevated pressure such that the combined overhead vapors from the two towers can supply all, or substantially all, of the heat requirements for the first stripper-rectifier tower 10 which is operated at a lower pressure than the towers 12 and 13. Similarly, the overhead vapors from the tower 10 supply all, or substantially all, of the heat requirements for the tower 11 which is operated at a lower pressure than the tower 10. The only heat input to the system under most circumstances is the steam supplied to the reboilers of the towers 12 and 13. Substantial energy savings are realized by the resultant triple effect steam usage since the heat associated with the condensation of overhead vapors replaces the steam which would ordinarily be used as the heat source for the stripper-rectifier tower in a conventional system.

Broadly speaking, the pressure in the towers 12 and 13 may be between about 100 to about 200 psig, while the towers 10 and 11 are operated from subatmospheric pressure up to about 100 psig with the pressure in the tower 10 being greater than the pressure in the tower 11. In a preferred embodiment of the invention, the towers 12 and 13 are operated at about 175 psig, the first stage tower 10 operates at about 50 psig, and the second stage tower 11 operates at atmospheric pressure. In another embodiment of the invention, the pressure levels can be reduced throughout the system so that the towers 12 and 13 operate at about 75 psig, the tower 10 operates at atmospheric pressure, and the tower 11 operates at subatmospheric pressure.

In the system illustrated in the drawings, the first stage stripper-rectifier tower 10 is shown as operating as an ethanol stripping tower only, and the overhead vapors from the tower 10, after condensation in the condenser-reboiler 107 are supplied to the tower 11 for further stripping and rectification to produce the intermediate spirits stream of 190° U.S. proof ethanol. Alternatively, however, the towers 10 and 11 can operate in parallel as stripping and rectifying towers, in which case an intermediate spirits stream of 190° U.S. proof ethanol is removed several trays below the top of each tower and the combined streams are supplied to the intermediate storage tank 156 for subsequent introduction into the dehydrating tower 12. In such parallel operation of the towers 10 and 11, fusel oil sidestreams are withdrawn from both the towers 10 and 11 and supplied to the cooler 136 and the washer-decanter 138.

Also in the preferred system illustrated in the drawings, both the dehydrating tower 12 and the azeotropic agent stripping tower 13 are operated at higher pressures than the towers 10 and 11. However, if desired, substantial energy savings can still be achieved by pressurizing the dehydrating tower 12 and operating the azeotropic agent stripping tower 13 at atmospheric pressure. In such case the overhead vapors in line 34 from the tower 13 will be condensed in a separate water cooled condenser (not shown) and the resultant condensate supplied to the decanter 53.

As previously pointed out, the multiple pressure level concept of the present invention has important advantages over the distillation systems heretofore proposed. For some feedstocks it is undesirable to pressurize the stripper-rectifier tower to the relatively high level required to obtain the advantages of multiple effect steam usage and heat reuse because the high pressures and resultant temperatures may cause polymerization and degradation of various components of the beer feedstock. However, by operating the dehydrating tower, and preferably also the azeotropic agent stripping tower, at higher pressures, in accordance with the present invention, the stripper-rectifier towers can be operated at lower pressure levels while still achieving substantial energy savings. Thus, the invention has the two-fold advantage of allowing substantial energy savings even when it is not desirable to pressurize the stripper-rectifier tower, and when the stripper-rectifier tower can be pressurized, the energy requirements can be reduced even further by employing the three pressure level concept using dual stripper-rectifier towers.

Although the maximum benefits of the invention are achieved by using a pair of stripper-rectifier towers operated at successively lower pressures than the dehydrating tower (or both the dehydrating and azeotropic agent stripping towers), substantial benefits can also be realized by the use of only a single stripper-rectifier, as might be the case when pressurization of the stripper-rectifier is undesirable. In a preferred embodiment of this modification of the invention, the pressurized dehydrating and azeotropic agent stripping towers may operate at about 100 psig, and the single stage stripper-rectifier tower may operate at atmospheric pressure or subatmospheric pressure.

The vapor-liquid equilibrium for ethanol-water systems is such that the use of a higher pressure in the first stage stripper-rectifier does not appreciably affect the separation of alcohol and water. Consequently, the first stage stripper-rectifier does not require an excessive number of distillation trays nor does it require appreciably more steam usage. The two stage stripper-rectifier arrangement can result in a saving of up to about 43% of the steam usage associated with the conventional distillation system.

The operation of the dehydrating tower 12 at elevated pressure does not seriously affect the separation of water from ethanol because of two counteracting phenomena. A beneficial effect of operating at higher pressures is a shift in the ternary azeotrope composition to a higher concentration of alcohol. However, a negative effect is the somewhat higher reflux ratio required to strip the azeotropic agent and water from the anhydrous ethanol bottoms product. Although pressurized operation of the dehydrating tower requires slightly more steam as compared to an atmospheric dehydrating tower, the additional heat is re-used in the first stage stripper-rectifier tower and the total steam usage is not adversely affected. For example, the steam savings associated with pressurized operation of the dehydrating and azeotropic agent stripping towers, in accordance with the system illustrated in the drawings, is from about 3 to about 6 pounds of steam per U.S. gallon of anhydrous ethanol as compared with the use of a pressurized stripper-rectifier tower system for ethanol recovery from a 6 wt.% ethanol feed as described in the Katzen et al U.S. Pat. No. 4,217,178.

In addition to the principal savings effected by pressurized operation of the dehydrating tower (or both the dehydrating and azeotropic stripping towers) and the resultant multiple effect steam usage, further savings are accomplished by preheating the beer feedstock by condensation of overhead vapors from the lower pressure stripper-rectifier tower 11 and also by means of the heat contained in the bottoms streams from the stripper-rectifier towers. Although heat can be recovered from these bottoms streams by indirect liquid-liquid heat exchange in the usual manner, it is advantageous to recover the heat from the bottoms streams by multi-stage flashing, in the manner illustrated in the drawings, when the bottoms streams contain suspended solids which tend to foul or plug conventional heat exchangers. This difficulty is overcome by the multi-stage flashing technique so that only the vapors from the flash drums are passed through the heat exchangers for preheating the feedstock. In addition, the illustrated system achieves additional heat economy by further flashing the higher pressure condensates collected from multi-stage flashing of the stripper-rectifier bottoms and also by flashing the steam condensates collected from the steam reboilers.

In a representative embodiment of the present invention using the system illustrated in the drawings with a dilute ethanol feedstock containing about 6 wt.% ethanol, and with about 60% of the feedstock being fed to the tower 10 and about 40% to the tower 11, the overall steam savings achieved is about 53% as compared with a conventional distillation system using a single stage stripper-rectifier tower, a dehydrating tower, and an azeotropic agent stripping tower, all operated at substantially atmospheric pressure. As compared to the system described in the Katzen et al U.S. Pat. No. 4,217,178, the process of the present invention results in a steam saving of about 25%.

Since the tower 10 is ordinarily operated under super-atmospheric pressure, it is preferred that the stripping section of at least the tower 10, and desirably both towers 10 and 11, utilize the baffle tray design and mode of operation described in British Pat. No. 1,310,544 and Canadian Pat. No. 876,620 in order to minimize scaling and fouling of the tower. In the aforesaid patents the section of the tower below the feed tray is provided with a plurality of vertically spaced baffles in the form of smooth surfaced plate members which are imperforate, except for specified relatively large open areas for the passage of fluids, and are free of the usual flow-obstructing protuberances such as weirs, seals, bubble caps, downcomers, and the like. The vapor-liquid contacting action is obtained in the vertical spaces between successive baffles.

Although other baffle designs may be used, the preferred structure comprises a "disk and donut" baffle configuration consisting of a plurality of vertically-spaced annular or ring-shaped baffle members and a plurality of circular or disk-shaped baffle members interposed in vertically spaced relation between the annular baffle members. The outer peripheries of the annular baffle members engage the inner surface of the tower and the inner peripheries or edges of these baffle members define circular open areas. The circular baffle members overlie and are in substantial axial alignment with the open areas in the adjacent annular baffle members. An annular open area is defined between the edge of each circular baffle member and the wall of the tower, and the open areas of adjacent baffle members are transversely offset so that the ascending gas or vapor phase must traverse a tortuous path with repeated changes of direction in passing upwardly through the open areas of the baffles.

The vertical space between successive baffles is such that the liquid phase which overflows the edges of the open areas of the baffles is contacted with a relatively high velocity gas or vapor phase so as to effect substantially complete dispersion of the down-flowing curtain of liquid into discrete droplets or an aerated liquid or froth, depending upon the surface tension relationship of the gas or vapor and the liquid. Thereafter, as the gas or vapor containing the entrained liquid droplets passes upwardly through the open areas of the baffles, the velocity is substantially decreased so that the major part of the liquid droplets will coalesce and drop back to the next lower baffle thereby keeping the net entrainment to a minimum. The separated gas or vapor, containing only a moderate amount of entrained liquid, then passes upwardly through the next vertical space between baffles and the dispersing or frothing effect is repeated. By means of the repeated velocity changes between successive sets of baffles, a multiplicity of contacts are effected whereby selected components of the gas or vapor will be transferred into the descending liquid or selected components of the liquid phase will be desorbed or stripped and transferred into the ascending gas or vapor stream.

In the preferred mode of operation of the baffle tray tower the flow rate of the gas or vapor phase is correlated with the vertical spacing between adjacent baffles and with the open areas of the baffles such that the horizontal velocity factor $f_h$ between adjacent baffles is within the range of from 0.20 to 0.80 feet per second and the vertical velocity factor $f_v$ in the open areas of the baffles is substantially less than the horizontal velocity factor $f_h$ and is also within the range of from 0.10 to 0.40 feet per second. The velocity factors are determined in accordance with the following equations:

$$f_h = U_h \left( \frac{\rho_v}{\rho_L - \rho_v} \right)^{\frac{1}{2}}$$

$$f_v = U_v \left( \frac{\rho_v}{\rho_L - \rho_v} \right)^{\frac{1}{2}}$$

where $U_v$ is the velocity in feet per second of the gas or vapor phase passing through the open areas of the baffles, $U_h$ is the velocity in feet per second of the gas or vapor phase passing through the descending liquid phase between adjacent baffles, $\rho_v$ is the density in pounds per cubic foot of the ascending gas or vapor phase at the temperature and pressure in the tower, and $\rho_L$ is the density in pounds per cubic foot of the descending liquid phase at the temperature in the tower. In general, the horizontal velocity factor will be on the order of twice the vertical velocity factor, and because of the intensive agitation caused by contact of rising vapors against descending liquid, the baffle trays are to a large extent self-cleaning so that interruption of operations is at a minimum.

Although the invention has been described with particular reference to the preferred embodiment illustrated in the drawing, it will be understood that various modifications may be made without departing from the scope of the invention as defined in the appended claims.

We claim:

1. In a distillation method for recovering anhydrous ethanol from a dilute ethanol-containing feedstock wherein the feedstock is introduced into a stripping and rectification section, a concentrated ethanol stream is removed from said stripping and rectification section and is introduced into a dehydrating tower, an azeotropic agent is also introduced into said dehydrating tower, a substantially azeotropic overhead is removed from said dehydrating tower, an anhydrous ethanol product is removed from the bottom portion of said dehydrating tower, the substantially azeotropic overhead from said dehydrating tower is condensed and separated into an upper phase rich in azeotropic agent and a lower water-rich phase, the upper phase is returned to said dehydrating tower, and the lower water-rich phase is introduced into an azeotropic agent stripping tower wherein the azeotropic agent is recovered and returned to the system;

the improvement which comprises the steps of:
(a) providing in said stripping and rectification section a first stage distillation tower comprising an ethanol stripping tower and a second stage distillation tower comprising a stripper-rectifier tower;
(b) preheating said feedstock;
(c) splitting the preheated feedstock into two preheated feed streams of unequal size;
(d) further preheating the larger of said feed streams;
(e) introducing said larger feed stream into the top portion of said first stage distillation tower;
(f) introducing the smaller of said feed streams into said second stage distillation tower;
(g) maintaining a higher pressure in said first stage distillation tower than in said second stage distillation tower;
(h) maintaining a higher pressure in said dehydrating tower than in said first stage distillation tower;
(i) condensing steam to supply the heat required in said dehydrating tower;
(j) supplying the heat required in said first stage distillation tower by condensing said substantially azeotropic overhead from said dehydrating tower;
(k) removing overhead ethanol-containing vapors from said first stage distillation tower and condensing said vapors to supply the heat required in said second stage distillation tower;
(l) introducing the condensate from step (k) into said second stage distillation tower;
(m) condensing overhead vapors from said second stage distillation tower;
(n) obtaining said concentrated ethanol stream by removing the same from the upper portion of said second stage distillation tower;
(o) withdrawing bottoms streams from said first and second stage distillation towers;
(p) said preheating of said feedstock in step (b) being effected first by means of the heat obtained in condensing step (m) and then by means of the heat contained in a bottoms stream withdrawn from at least the first of said first and second stage distillation towers; and
(q) said further preheating of said larger feed stream in step (d) being effected by means of the heat contained in the bottoms stream withdrawn from said first stage distillation tower.

2. The method of claim 1 further characterized by maintaining higher pressures both in said dehydrating tower and in said azeotropic agent stripping tower than in said first stage distillation tower, condensing steam to supply the heat required both in said dehydrating tower and in said azeotropic agent stripping tower, removing overhead vapors containing said azeotropic agent from said azeotropic agent stripping tower, and condensing said substantially azeotropic overhead from said dehydrating tower and said overhead vapors from said azeotropic agent stripping tower to supply the heat required in said first stage distillation tower.

3. The method of claim 1, wherein said larger feed stream comprises more than 50 wt.% but not more than about 70 wt.% of the total feedstock and said smaller feed stream comprises less than 50 wt.% but not less than about 30 wt.% of the total feedstock.

4. The method of claim 1, wherein the condensate from step (m) is returned as reflux to said second stage distillation tower, except for the removal of a heads draw to avoid accumulation of low-boiling impurities in said anhydrous ethanol product.

5. The method of claim 1, wherein at least one fusel oil side draw containing higher boiling impurities is removed from an intermediate portion of said second stage distillation tower, said fusel oil side draw is washed with water, a fusel oil layer is separated from an aqueous ethanol-containing layer, and said aqueous ethanol-containing layer is returned to said second stage distillation tower.

6. The method of claim 1, wherein the pressure in said dehydrating tower is from about 100 to about 200 psig, and the pressure in said distillation towers is from subatmospheric pressure to about 100 psig.

7. The method of claim 2, wherein the pressure in said dehydrating and azeotropic agent stripping towers is about 175 psig, the pressure in said first stage distillation tower is about 50 psig, and the pressure in said second stage distillation tower is about atmospheric pressure.

8. The method of claim 1, wherein said larger feed stream is degassed prior to being introduced into said first stage distillation tower, and the removed gases are introduced into the lower portion of said second stage distillation tower.

9. The method of claim 1, wherein said feedstock is preheated in step (p) by means of the heat contained in the bottoms streams withdrawn from both said first and second stage distillation towers.

10. The method of claim 1, wherein in step (p) said bottoms stream from said first stage distillation tower is flashed in a plurality of successive bottoms flash stages and said feedstock is preheated in a plurality of successive heat exchange steps with the flash vapors from the respective bottoms flash stages.

11. The method of claim 10, wherein a bottoms stream from said second stage distillation tower is also flashed in one of said bottoms flash stages subsequent to the first bottoms flash stage.

12. The method of claim 2, wherein the preheating steps are carried out as follows:

said feedstock is preheated first by means of heat obtained in condensing step (m);

said feedstock is further preheated by heat exchange with flash vapors obtained by flashing steam condensate from the heating of said dehydrating tower and said azeotropic agent stripping tower;

said bottoms stream from said first stage distillation tower is flashed in a plurality of successive bottoms flash stages;

said bottoms stream from said second stage distillation tower is flashed in one of said bottoms flash stages subsequent to the first bottoms flash stage;

the flash vapors from said bottoms flash stages are separately condensed in a plurality of heat exchange steps;

said feedstock is further preheated by heat exchange with flash vapors obtained by further flashing the combined condensates from said plurality of heat exchange steps and then by successive heat exchange in corresponding heat exchange steps with the flash vapors from said bottoms flash stages subsequent to said first bottoms flash stage;

said feedstock is then split into two feed streams of unequal size;

the larger of said feed streams is further preheated by heat exchange in the corresponding heat exchange step with the flash vapors from said first bottoms flash stage and is then introduced into said first stage distillation tower; and the smaller of said feed streams is introduced into said second stage distillation tower.

13. The method of claim 12, wherein said larger feed stream is degassed after being further preheated and prior to being introduced into said first stage distillation tower, and the removed gases are introduced into the lower portion of said second stage distillation tower.

14. In a distillation method for recovering anhydrous ethanol from a dilute ethanol-containing feedstock that also contains dissolved gases, wherein the feedstock is introduced into a stripping and rectification section, a concentrated ethanol stream is removed from said stripping and rectification section and is introduced into a dehydrating tower, an azeotropic agent is also introduced into said dehydrating tower, a substantially azeotropic overhead is removed from said dehydrating tower, an anhydrous ethanol product is recovered from the bottom portion of said dehydrating tower, the substantially azeotropic overhead from said dehydrating tower is condensed and separated into an upper phase rich in azeotropic agent and a lower water-rich phase, the upper phase is returned to said dehydrating tower, and the lower water-rich phase is introduced into an azeotropic agent stripping tower wherein the azeotropic agent is recovered and returned to the system; the improvement which comprises the steps of:

(a) providing in said stripping and rectification section a first stage distillation tower comprising an ethanol stripping tower and a second stage distillation tower comprising a stripper-rectifier tower;

(b) preheating and splitting the feedstock to provide a preheated larger feed stream and a preheated smaller feed stream;

(c) degassing said preheated larger feed stream and introducing the removed gases into the lower portion of said second stage distillation tower;

(d) introducing the degassed larger feed stream into the top portion of said first stage distillation tower;

(e) introducing said preheated smaller feed stream into said second stage distillation tower;

(f) maintaining a higher pressure in said first stage distillation tower than in said second stage distillation tower;

(g) maintaining a higher pressure in said dehydrating tower than in said first stage distillation tower;

(h) condensing steam to supply the heat required in said dehydrating tower;

(i) supplying the heat required in said first stage distillation tower by condensing said substantially azeotropic overhead from said dehydrating tower;

(j) removing overhead ethanol-containing vapors from said first stage distillation tower and condensing said vapors to supply the heat required in said second stage distillation tower;

(k) introducing the condensate from step (j) into said second stage distillation tower; and (l) obtaining said concentrated ethanol stream by removing the same from the upper portion of said second stage distillation tower.

15. The method of claim 14, further characterized by maintaining higher pressures both in said dehydrating tower and in said azeotropic agent stripping tower than in said first stage distillation tower, condensing steam to supply the heat required both in said dehydrating tower and in said azeotropic agent stripping tower, removing overhead vapors containing said azeotropic agent from said azeotropic agent stripping tower, and condensing said substantially azeotropic overhead from said dehydrating tower and said overhead vapors from said azeotropic agent stripping tower to supply the heat required in said first stage distillation tower.

16. The method of claim 14, wherein said preheating of said feedstock is effected first by means of the heat obtained by condensation of overhead vapors from said second stage distillation tower and thereafter by means of the heat contained in a bottoms stream withdrawn from at least the first of said first and second stage distillation towers.

17. The method of claim 14, wherein said degassing in step (c) is effected by introducing said preheated larger feed stream into a degassing vessel, and introducing steam into said degassing vessel and thereby removing said dissolved gases from said larger feed stream.

18. In an apparatus for recovering anhydrous ethanol from a dilute ethanol-containing feedstock including a stripping and rectification section, a dehydrating tower adapted to be operated at a higher pressure than said stripping and rectification section, an azeotropic agent stripping tower, means for introducing the dilute ethanol-containing feedstock into said stripping and rectification section, means for removing a concentrated ethanol stream from said stripping and rectification section and introducing the same into said dehydrating tower, means for introducing an azeotropic agent into said dehydrating tower, means for removing a substantially azeotropic overhead from said dehydrating tower, means for removing an anhydrous ethanol product from the bottom portion of said dehydrating tower, means for condensing said substantially azeotropic overhead, means for separating the resultant condensate into an upper phase rich in said azeotropic agent and a lower water-rich phase, means for returning said upper phase to said dehydrating tower, means for introducing said lower phase into said azeotropic agent stripping tower, and means for recovering said azeotropic agent from said azeotropic agent stripping tower and returning the same to said dehydrating tower;

the improvement wherein:

said stripping and rectification section comprises a first stage distillation tower comprising an ethanol stripping tower and a second stage distillation tower comprising a stripper-rectifier tower, said first stage distillation tower being adapted to be operated at a higher pressure than said second stage distillation tower;

said apparatus further includes means for preheating said feedstock; means for splitting the preheated feedstock into two preheated feed streams of unequal size; means for further preheating the larger of said feed streams; means for introducing said larger feed stream into the top portion of the said first stage distillation tower; means for introducing the smaller of said feed streams into said second stage distillation tower; means for condensing steam to supply the heat required in said higher pressure dehydrating tower; first condenser-reboiler means connected to said first stage distillation tower; means for introducing said substantially azeotropic overhead from said dehydrating tower into said first condenser-reboiler means, whereby the heat required in said first stage distillation tower is supplied by condensation of said substantially azeotropic overhead from said higher pressure dehydrating tower; second condenser-reboiler means connected to said second stage distillation tower; means for removing overhead ethanol-containing vapors from the higher pressure first stage distillation tower and introducing them into said second condenser-reboiler means for supplying the heat required in said second stage distillation tower; means for introducing the condensate from said second condenser-reboiler means into said second stage distillation tower; and means for withdrawing bottoms streams from said first and second stage distillation towers;

said means for removing a concentrated ethanol stream comprises means for withdrawing a concentrated ethanol stream from the upper portion of said second stage distillation tower;

said means for preheating said feedstock comprises condenser-preheater means for condensing overhead vapors from said second stage distillation tower; means for passing said feedstock, prior to splitting thereof, in heat exchange relation through said condenser-preheater means for initially preheating said feedstock; and heat exchange means for further preheating said feedstock by the heat contained in a bottoms stream withdrawn from at least the first of said first and second stage distillation towers; and said means for further preheating said larger feed stream comprises heat exchange means for effecting said further preheating by the heat contained in the bottoms stream withdrawn from said first stage distillation tower.

19. The apparatus of claim 18, wherein said azeotropic agent stripping tower is also adapted to be operated at a higher pressure than said stripping and rectification section, said apparatus further including means for condensing steam to supply the heat required in said higher pressure azeotropic agent stripping tower, and means for introducing overhead vapors from said azeotropic agent stripping tower into said first condenser-reboiler means, whereby the heat required in said first stage distillation tower is supplied by condensation of both said substantially azeotropic overhead from said dehydrating tower and said overhead vapors from said azeotropic agent stripping tower.

* * * * *